US012738057B2

(12) United States Patent
Patel et al.

(10) Patent No.: US 12,738,057 B2
(45) Date of Patent: Sep. 15, 2026

(54) CUT-PASTE TRAINING AUGMENTATION FOR MACHINE LEARNING MODELS

(71) Applicant: NEC Laboratories America, Inc., Princeton, NJ (US)

(72) Inventors: Deep Patel, Franklin Park, NJ (US); Giovanni Milione, Monmouth Junction, NJ (US); Kai Li, Plainsboro, NJ (US); Farley Lai, Santa Clara, CA (US); Erik Kruus, Hillsborough, NJ (US)

(73) Assignee: NEC Corporation, Tokyo (JP)

( * ) Notice: Subject to any disclaimer, the term of this patent is extended or adjusted under 35 U.S.C. 154(b) by 249 days.

(21) Appl. No.: 18/439,242

(22) Filed: Feb. 12, 2024

(65) Prior Publication Data

US 2024/0273902 A1 Aug. 15, 2024

Related U.S. Application Data

(60) Provisional application No. 63/445,049, filed on Feb. 13, 2023.

(51) Int. Cl.

| | |
|---|---|
| ***G06V 20/40*** | (2022.01) |
| ***G06V 10/776*** | (2022.01) |
| ***G06V 40/20*** | (2022.01) |
| ***G16H 30/40*** | (2018.01) |

(52) U.S. Cl.

CPC ............ *G06V 20/44* (2022.01); *G06V 10/776* (2022.01); *G06V 40/20* (2022.01); *G16H 30/40* (2018.01)

(58) Field of Classification Search

None

See application file for complete search history.

(56) References Cited

U.S. PATENT DOCUMENTS

| | | | | |
|---|---|---|---|---|
| 2022/0096003 | A1* | 3/2022 | Mai | H04L 25/0224 |
| 2022/0180173 | A1* | 6/2022 | Jonnalagadda | G06N 3/04 |
| 2024/0135973 | A1* | 4/2024 | Bai | G11B 27/031 |
| 2024/0424245 | A1* | 12/2024 | Guest | G16H 20/60 |

OTHER PUBLICATIONS

Ghiasi et al., "Simple Copy-Paste is a Strong Data Augmentation Method for Instance Segmentation", arXiv:2012.07177v2 [cs.CV] Jun. 23, 2021, pp. 1-13.

* cited by examiner

*Primary Examiner* — Wei Wen Yang

(74) *Attorney, Agent, or Firm* — Vincent Duffy

(57) ABSTRACT

Methods and systems of training a machine learning model include identifying an object or person related to an action in a first video. The object or person is copied from the first video to a second video to generate a third video. A machine learning model is trained using the first video and the third video.

20 Claims, 9 Drawing Sheets

CUT-PASTE TRAINING AUGMENTATION FOR MACHINE LEARNING MODELS

RELATED APPLICATION INFORMATION

This application claims priority to 63/445,049, filed on Feb. 13, 2023, incorporated herein by reference in its entirety.

BACKGROUND

Technical Field

The present invention relates to machine learning systems and, more particularly, to augmenting training datasets for machine learning systems.

Description of the Related Art

Machine learning models, such as those which perform action recognition on video streams, make use of training datasets that include videos showing a variety of actions. However, training data for uncommon events in different environments may not be readily available. For example, while video of a person walking may be commonly available in training datasets, video of a person falling is comparatively rare. Video showing such rare actions may not be available for all environments.

Models that are trained on a given dataset may suffer from reduced accuracy when deployed in a different environment, causing an increased number of false positives due to inherent scene and object biases in the training data. For example, this may be due to large differences between the distribution of training dataset images and the images in the target scene in terms of scene complexity, lighting, camera angles, and field of view.

SUMMARY

A method of training a machine learning model includes identifying an object or person related to an action in a first video. The object or person is copied from the first video to a second video to generate a third video. A machine learning model is trained using the first video and the third video.

A system for training a machine learning model includes a hardware processor and a memory that stores a computer program. When executed by the hardware processor, the computer program causes the hardware processor to identify an object or person related to an action in a first video, to copy the object or person from the first video to a second video to generate a third video, and to train a machine learning model using the first video and the third video.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Training datasets can be augmented to increase the representation of rare occurrences in new environments. For example, an example of a rare action from a first video, set in a first environment, may be copied into a second video that is set in a second environment. This generates new videos in the second environment for the rare actions or events, thereby reducing the cost of data collection as well as improving the overall action recognition performance by addressing the problem of scene bias. Video examples can also be generated by adding specific artifacts and objects that can resolve the issue of object bias. Fine-tuning or training a model with the augmented dataset causes the model to learn important biases that are needed to detect actions and avoid other shortcuts in the training data.

Figure 1:
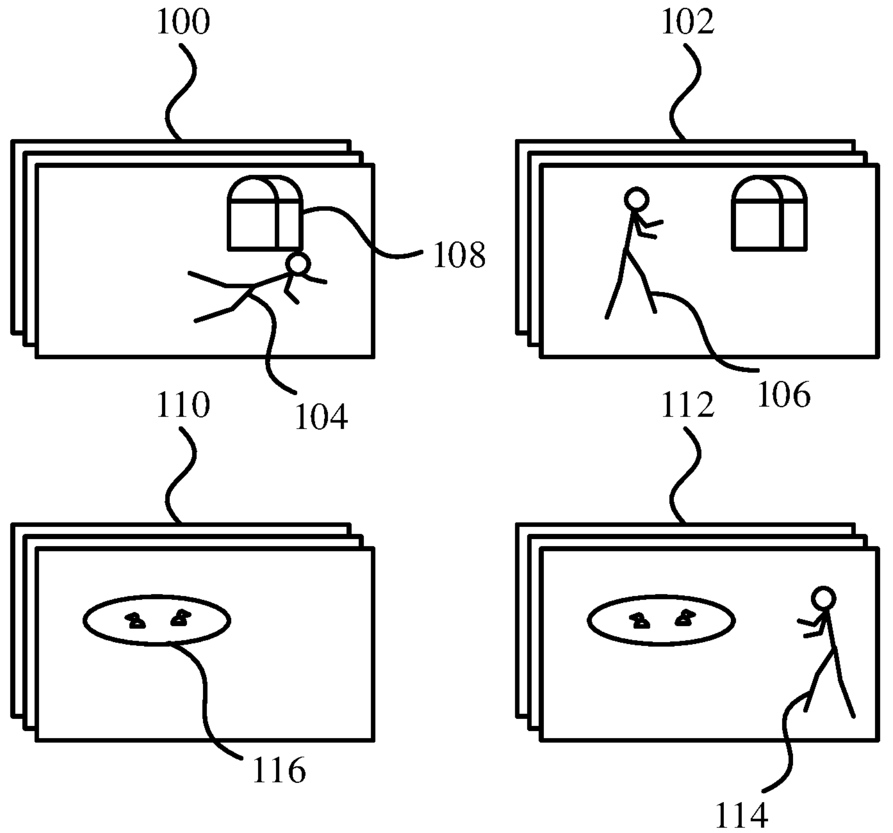
FIG. 1 is a diagram showing a set of videos in a training dataset for an action recognition model, in accordance with an embodiment of the present invention.

Referring now to FIG. 1, a set of different videos is shown. A first video 100 shows a relatively uncommon event 104 taking place, in this case illustrated as a person falling down. A second video 102 shows a relatively common event 106 taking place, in this case illustrated as a person walking normally. The first video 100 and the second video 102 illustrate the same first environment, and include one or more objects 108. The objects 108 may be involved in the event, or they may independent or background objects.

A third video 110 is shown of a second environment, distinct in at least one way from the first environment. In this example, the second environment shows a different scene entirely from the first environment, but in some cases the two environments may share features, such as a partially overlapping field of view. A fourth video 112 shows the same second environment as the third video 110, and includes a relatively common event 114.

These videos may be used to train a machine learning classifier, for example to recognize an action or event taking place within an input video. The resulting machine learning classifier may be used in the first environment or second environment, but it may have difficulty identifying events that are only represented in the training dataset in a different environment. For example, the trained machine learning classifier may have difficulty identifying falling events in the second environment, because that event is not represented in the second environment within the training dataset.

Figure 2:
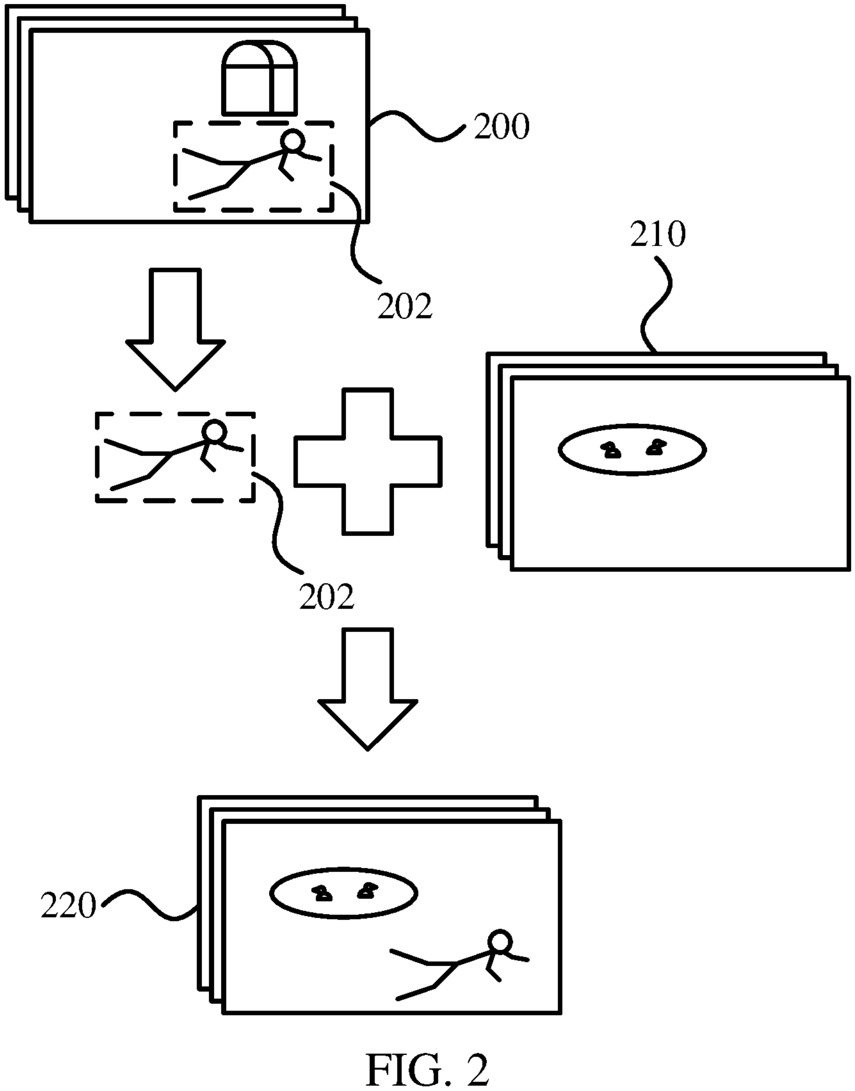
FIG. 2 is a diagram showing cut-paste augmentation of a training dataset to include an uncommon action in a new environment, in accordance with an embodiment of the present invention.

Referring now to FIG. 2, a combination of video elements is shown to augment the training dataset. A cut event 202 is identified within a source video 200, showing a first environment. The cut event 202 is extracted from the source video 200, for example by identifying an object or figure performing the action within a series of frames of the source video and copying the object or figure as a set of respective sub-frames.

The cut event 202 is then added to a target video 210. The target video 210 may depict a second environment, different from the first environment, and may include a different event or may include no event at all. The cut event 202 may be added to the target video 210 by pasting the sub-frames of the cut event 202 into respective frames of the target video 210. The result of this combination is an augmented video 220 that shows the cut event 202 within the second environment. Adding the augmented video 220 to the training dataset results in a trained model that shows superior performance when attempting to identify the cut event 202 within the second environment.

Figure 3:
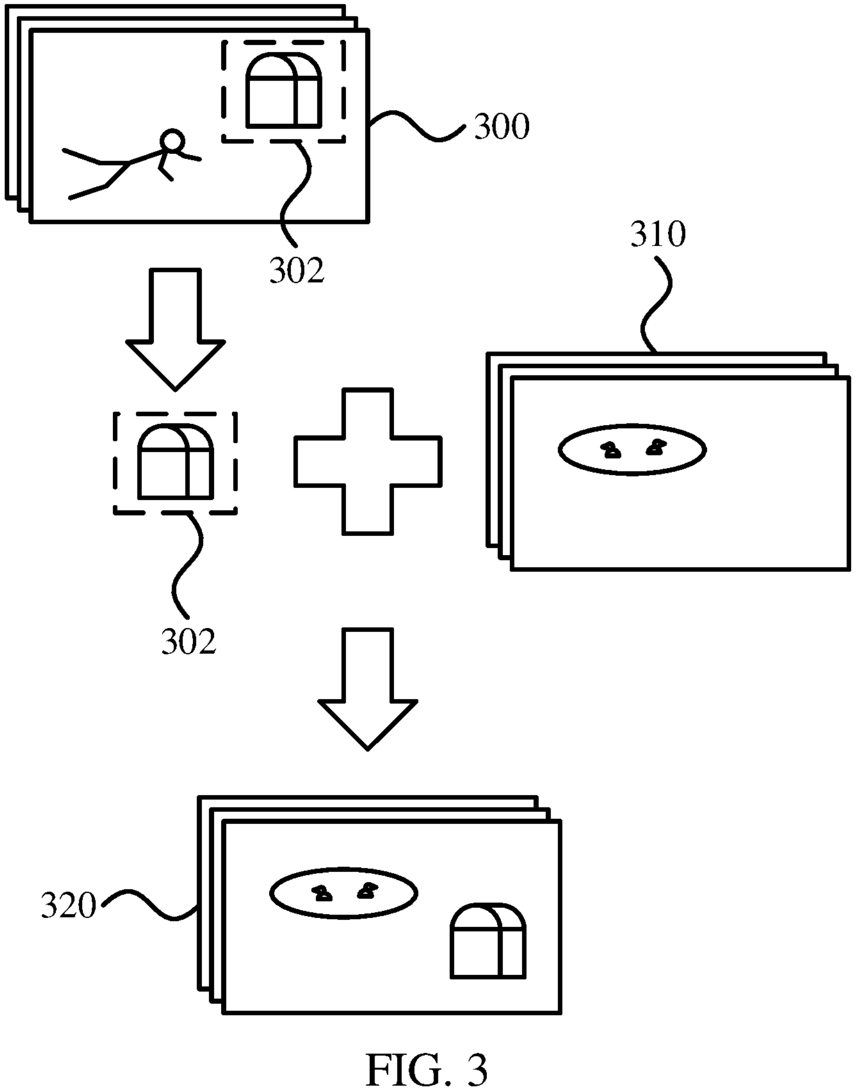
FIG. 3 is a diagram showing cut-paste augmentation of a training dataset to combat object bias in the trained model, in accordance with an embodiment of the present invention.

Referring now to FIG. 3, a combination of video elements is shown to augment the training dataset. An object cutout 302 is identified within a source video 300, showing a first environment. The object cutout 302 is extracted from the source video 300, for example by identifying an object or figure based on semantic segmentation within a series of frames of the source video and copying the object or figure as a set of respective sub-frames.

The object cutout 302 is then added to a target video 310. The target video 310 may depict a second environment, different from the first environment, and may include a different event or may include no event at all. The object cutout 302 may be added to the target video 310 by pasting the sub-frames of the object cutout 302 into respective frames of the target video 310. The result of this combination is an augmented video 320 that shows the object cutout 302 within the second environment. Adding the augmented video 320 to the training dataset may help combat biases in the trained model, which could otherwise identify the object with particular actions and therefore generate false positives when such an object is detected in a scene. This augmentation provides videos where the object in question is present in a scene without the associated action or event.

Objects that are associated with model biases can be identified by evaluating false—positive predictions—those which the classifier says include a given action, but which actually do not. In some cases this may be evaluated during operation by a human operator. In other cases, it may be detected by creating augmented video that includes a given object without the associated action. A gradient map of the model with respect to the augmented video may be used to determine whether the model is focusing before making the prediction. The gradient map can be computed using a backward pass of the model.

Figure 4:
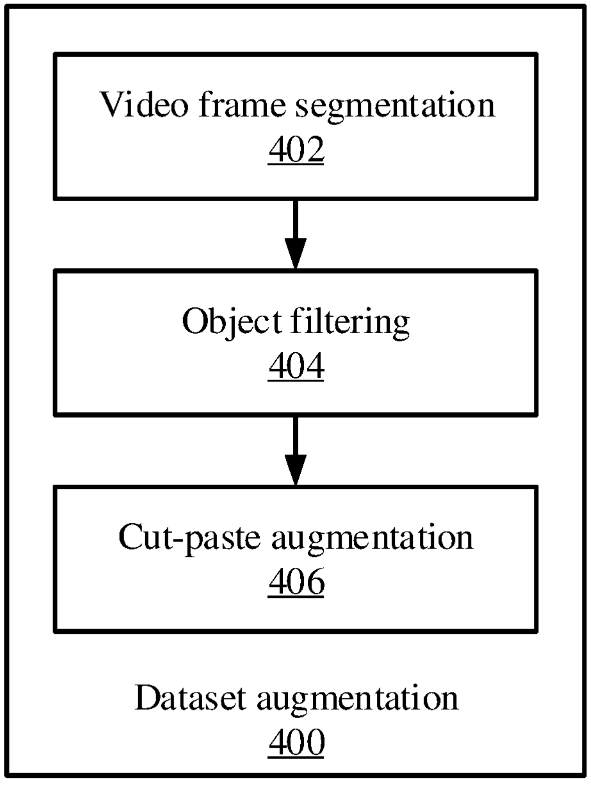
FIG. 4 is a block/flow diagram of a method for augmenting a training dataset, in accordance with an embodiment of the present invention.

Referring now to FIG. 4, a method of performing dataset augmentation is shown. Given a set of labeled training videos, block 402 performs video frame segmentation. The video frame segmentation 402 extracts semantic segmentation information from the labeled videos to provide, for example, pixel-wise classification of every object in a given scene. The segmentation information may include a person or object mask that identifies the location of the detected person or object within a given video frame.

Block 404 performs object filtering to remove the segmentation data for each frame based on known model biases and the target task for the system. Semantic information from the video frame segmentation 402 is used to generate cutouts of relevant objects and persons based on the needs of the training data. In some cases, the object filtering may remove all non-person object masks, keeping only person cut-outs from the video to generate videos with actions that include person or person-person interactions only. Such actions may include, e.g., running, walking, jumping, dancing, etc. In some embodiments, the object filtering may keep certain object and person masks within specified size and scale ranges, for example by considering he field of view of the target scene videos. The object filtering may thereby ignore masks that do not satisfy the constraints.

Block 406 performs augmentation of the training dataset by adding actions to a video in a new environment. For example, the augmentation may take video frames of a target scene and may add previously extracted object cutouts, for example derived from object filtering 404, to generate a new video. These custom object cutouts may be selected based on the type of bias of the action recognition model. For example, if a model always predicts identifies the action of "working on a computer" when there is a laptop or computer in the scene, the new video may be generated by including relevant objects instead of including the action.

Following this example, object cutouts featuring a laptop or desktop computer may be added without adding the corresponding person cutout that would indicate the action of "working." Adding such videos to the training dataset can counteract existing biases, where the presence of a particular object would otherwise cause the model to generate a false positive for an associated action.

In some embodiments, the cut-paste augmentation 406 can scale an object or person mask according to the height and width of the target frames of the new video, overlaying the cutouts onto the target frames to generate new videos that have rare actions or events in the new target scene. In some embodiments, the cut-paste augmentation 406 can be performed using a deep learning model based on a generative adversarial network or a diffusion model. Such a model may be trained to generate perceptually realistic videos by combining the cutouts and the target videos. A diffusion probabilistic model in particular can be trained in a conditioned way. Custom object cutouts and filtered person and object cutouts can be used to condition the diffusion model to generate temporally and spatially consistent frames.

The cut-paste augmentation 406 may add appropriate labels to the augmented videos. For example, a person cutout that shows a person performing a given action may have a label that is taken from a source video for the cutout. Thus, for a source video that is labeled as showing the "falling down" action, the person cutout may be assigned the same label. When person the cutout is then added to the new video, the new video may similarly be labeled as showing the "falling down" action. In the event that an object cutout is used to mitigate model object bias, the label of the associated action may be omitted or excluded from the labels for the new video. This helps to establish that the model should not necessarily associate the presence of the object with the action.

Figure 5:
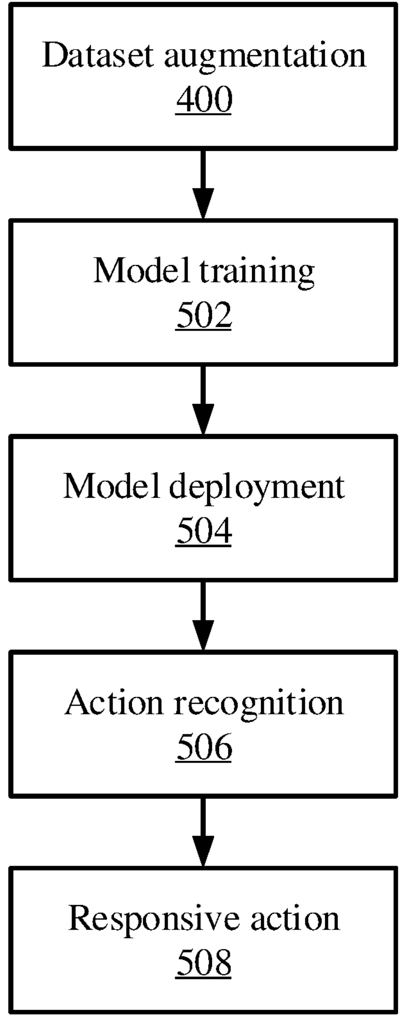
FIG. 5 is a block/flow diagram of a method for training and using an action recognition model, in accordance with an embodiment of the present invention.

Referring now to FIG. 5, a method of training and using an action recognition model is shown. As described above, dataset augmentation 400 enhances an existing training dataset, for example by adding rate actions or events to videos from an environment that lacks them or by adding objects to videos in instances where the object's association with a particular action biases the model. The result of dataset augmentation 400 may be a combined training dataset that includes original training examples as well as augmented training examples.

Block 502 performs training of a machine learning model using the enhanced training dataset. It is specifically contemplated that supervised training may be performed, using labels of the enhanced training dataset. In this example, the model may be trained to perform action recognition on input videos. By training the model with the enhanced training dataset, the model is made to be more robust. The resulting model will provide more accurate results for rare actions in a variety of environments, and furthermore will be less vulnerable to bias in instances when an object is present without an associated action taking place.

In some cases, blocks 400 and 502 may be repeated before deployment 504. For example, after model training 502, the trained model may be tested for biases associated with particular objects. A video including such an object may be provided as input to the model, and the output may be evaluated to determine whether the model generates a false positive for an action due to the presence of the object. If such a bias is detected, dataset augmentation 400 may be repeated to generate new videos that include the object and that do not include the associated action.

The model is deployed 504 to an operational environment. For example, the model may be deployed to a security system or hospital, where it may be used to monitor the actions performed by individuals. Action recognition 506 is then performed at the operational environment, with new video being collected and processed by the trained model. The action recognition may be used for any appropriate purpose, such as identifying risky behavior or adverse health events in a patient. A responsive action 508 may then be performed, for example by automatically summoning security personnel or by automatically administering a treatment to the patient.

Figure 6:
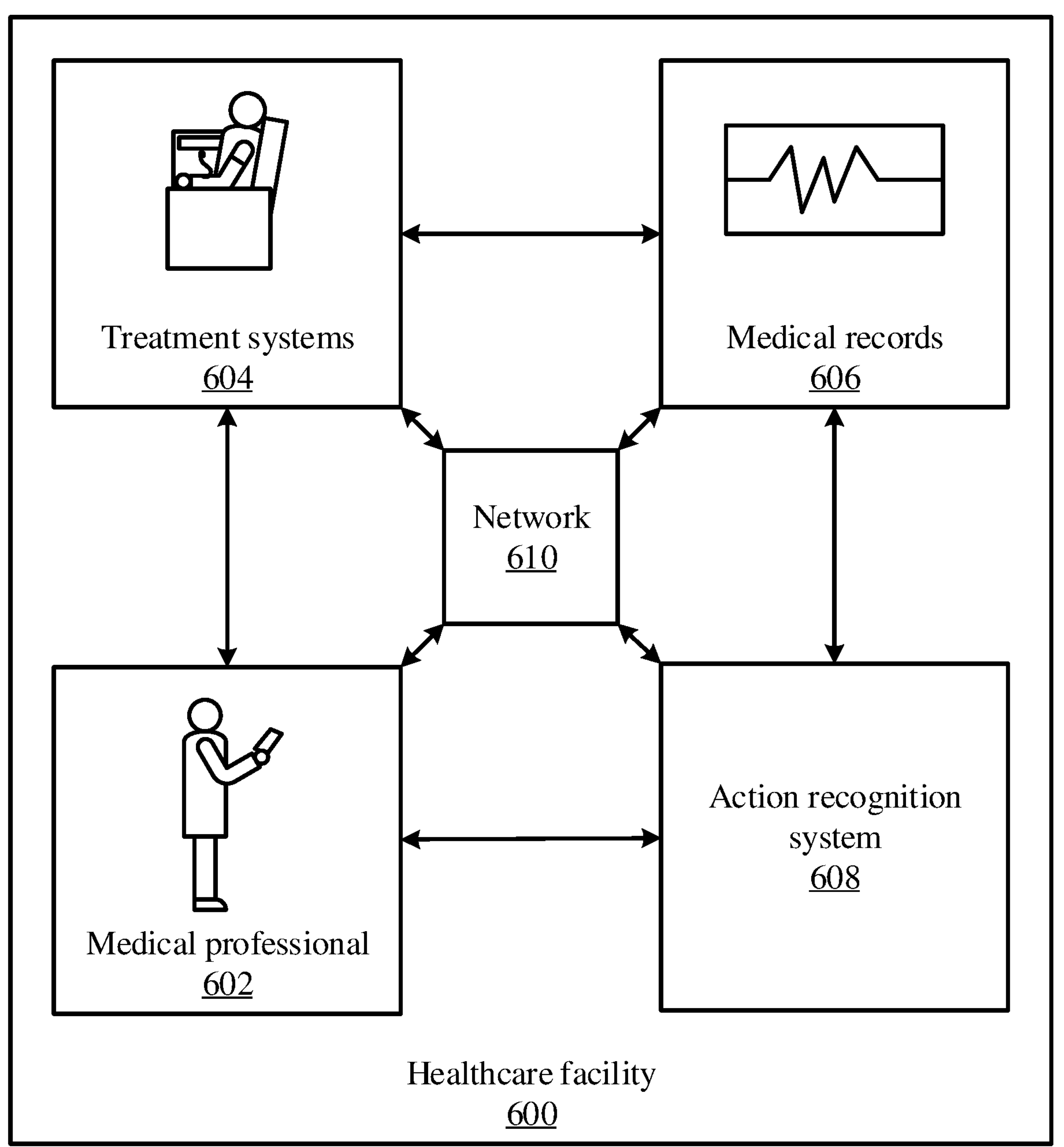
FIG. 6 is a block diagram showing a healthcare facility where action recognition is used to inform patient treatment, in accordance with an embodiment of the present invention.

Referring now to FIG. 6, a diagram of action recognition is shown in the context of a healthcare facility 600. Action recognition may be used in the context of the healthcare facility 600 to identify the actions performed by a patient, which can aid in devising a treatment for the patient. For example, video monitoring of the patient and subsequent action recognition may show that the patient is in distress or is experiencing a negative health event, such as a fall or a stroke. A treatment may be automatically triggered or administered to aid the patient.

The healthcare facility may include one or more medical professionals 602 who provide information relating to events and measurements of system status to action recognition system 608. Treatment systems 604 may furthermore monitor patient status to generate medical records 606 and may be designed to automatically administer and adjust treatments as needed. In some cases, the medical records 606 may include video monitoring of a patient.

Based on information drawn from at least the medical professionals 602, treatment systems 604, and medical records 606, action recognition system 608 identifies actions and events relating to the patient, particularly identifying an action relating to an abnormality in the health condition of the patient. Information about the recognized action may be forwarded to medical professionals 602 to diagnose and treat patient conditions.

The different elements of the healthcare facility 600 may communicate with one another via a network 610, for example using any appropriate wired or wireless communications protocol and medium. Thus the action recognition system 608 may access remotely stored medical records 606, may communicate with the treatment systems 604, and may receive instructions and send reports to medical professionals 602. In particular, the action recognition system 608 may automatically trigger treatment changes for a patient, responsive to new information gleaned from the medical records 606, by sending instructions to the treatment systems 604. For example, the treatment systems may automatically administer a drug or shut down treatment responsive to a negative health event.

In some cases, the action recognition system 608 may trigger a treatment for the patient responsive to a particular recognized action or event. Using the example of detecting that the patient is having a stroke, the treatment systems 604 may adjust dosage of automatically administered antiepileptic medications. The output of the action recognition system 608 may therefore include one or a combination of the above automatic treatments and notifying medical professionals 602. In some cases, the treatment plan may be used by a medical professional to assist in decision-making for patient management. For example, upon being informed of a change in a patient's condition, the healthcare professional 602 may go to the patient to check on them.

Figure 7:
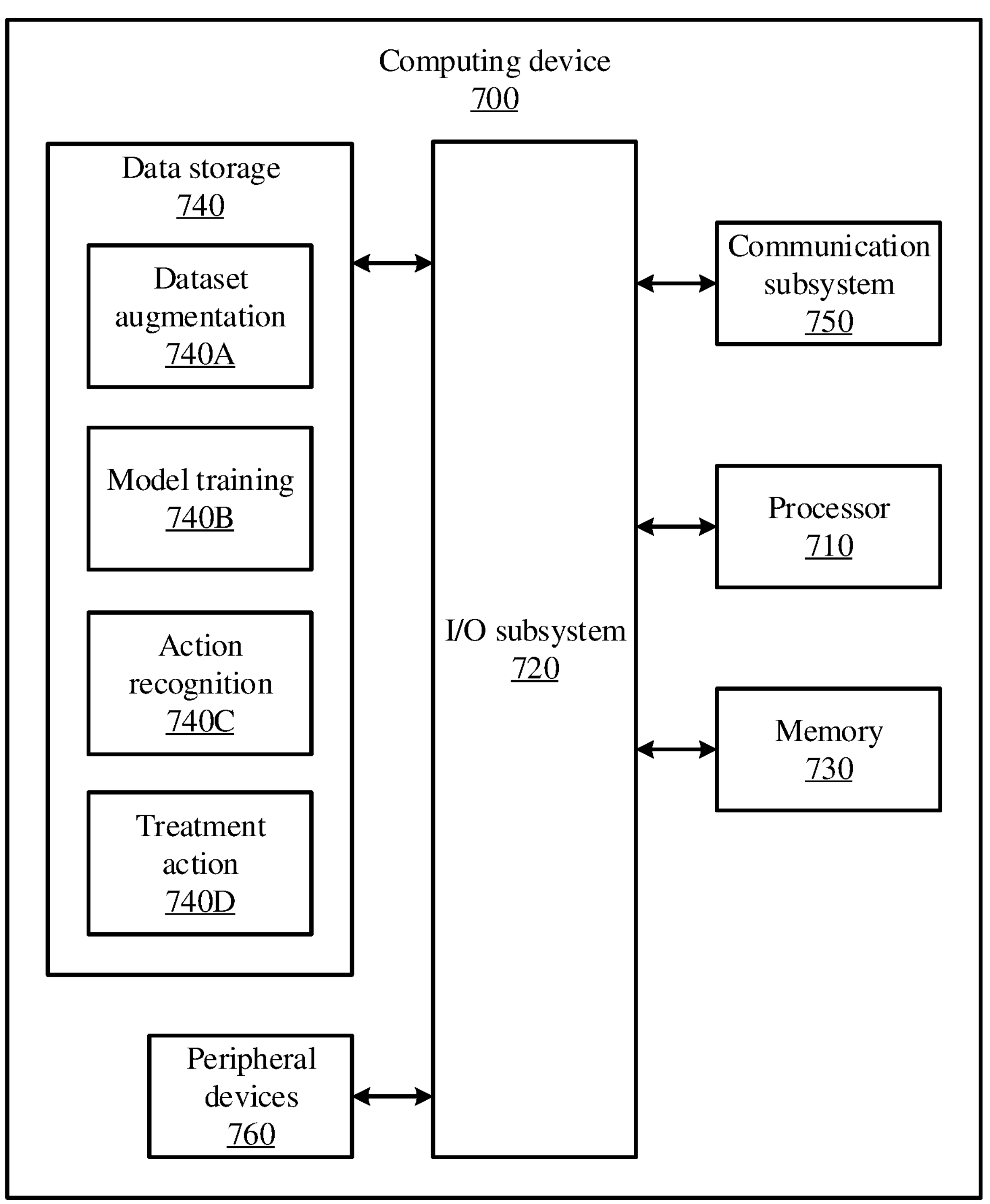
FIG. 7 is a block diagram of a computing device that can perform dataset augmentation, model training, and action recognition, in accordance with an embodiment of the present invention.

Referring now to FIG. 7, an exemplary computing device 700 is shown, in accordance with an embodiment of the present invention. The computing device 700 is configured to perform action recognition.

The computing device 700 may be embodied as any type of computation or computer device capable of performing the functions described herein, including, without limitation, a computer, a server, a rack based server, a blade server, a workstation, a desktop computer, a laptop computer, a notebook computer, a tablet computer, a mobile computing device, a wearable computing device, a network appliance, a web appliance, a distributed computing system, a processor-based system, and/or a consumer electronic device. Additionally or alternatively, the computing device 700 may be embodied as one or more compute sleds, memory sleds, or other racks, sleds, computing chassis, or other components of a physically disaggregated computing device.

As shown in FIG. 7, the computing device 700 illustratively includes the processor 710, an input/output subsystem 720, a memory 730, a data storage device 740, and a communication subsystem 750, and/or other components and devices commonly found in a server or similar computing device. The computing device 700 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 730, or portions thereof, may be incorporated in the processor 710 in some embodiments.

The processor 710 may be embodied as any type of processor capable of performing the functions described herein. The processor 710 may be embodied as a single processor, multiple processors, a Central Processing Unit(s) (CPU(s)), a Graphics Processing Unit(s) (GPU(s)), a single or multi-core processor(s), a digital signal processor(s), a microcontroller(s), or other processor(s) or processing/controlling circuit(s).

The memory 730 may be embodied as any type of volatile or non-volatile memory or data storage capable of performing the functions described herein. In operation, the memory 730 may store various data and software used during operation of the computing device 700, such as operating systems, applications, programs, libraries, and drivers. The memory 730 is communicatively coupled to the processor 710 via the I/O subsystem 720, which may be embodied as circuitry and/or components to facilitate input/output operations with the processor 710, the memory 730, and other components of the computing device 700. For example, the I/O subsystem 720 may be embodied as, or otherwise include, memory controller hubs, input/output control hubs, platform controller hubs, integrated control circuitry, firmware devices, communication links (e.g., point-to-point links, bus links, wires, cables, light guides, printed circuit board traces, etc.), and/or other components and subsystems to facilitate the input/output operations. In some embodiments, the I/O subsystem 720 may form a portion of a system-on-a-chip (SOC) and be incorporated, along with the processor 710, the memory 730, and other components of the computing device 700, on a single integrated circuit chip.

The data storage device 740 may be embodied as any type of device or devices configured for short-term or long-term storage of data such as, for example, memory devices and circuits, memory cards, hard disk drives, solid state drives, or other data storage devices. The data storage device 740 can store program code 740A for dataset augmentation, 740B for model training, 740C for action recognition, and/or 740D for performing a corrective action responsive to a recognized action. Any or all of these program code blocks may be included in a given computing system. The communication subsystem 750 of the computing device 700 may be embodied as any network interface controller or other communication circuit, device, or collection thereof, capable of enabling communications between the computing device 700 and other remote devices over a network. The communication subsystem 750 may be configured to use any one or more communication technology (e.g., wired or wireless communications) and associated protocols (e.g., Ethernet, InfiniBand®, Bluetooth®, Wi-Fi®, WiMAX, etc.) to effect such communication.

As shown, the computing device 700 may also include one or more peripheral devices 760. The peripheral devices 760 may include any number of additional input/output devices, interface devices, and/or other peripheral devices. For example, in some embodiments, the peripheral devices 760 may include a display, touch screen, graphics circuitry, keyboard, mouse, speaker system, microphone, network interface, and/or other input/output devices, interface devices, and/or peripheral devices.

Of course, the computing device 700 may also include other elements (not shown), as readily contemplated by one of skill in the art, as well as omit certain elements. For example, various other sensors, input devices, and/or output devices can be included in computing device 700, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized. These and other variations of the processing system 700 are readily contemplated by one of ordinary skill in the art given the teachings of the present invention provided herein.

Figure 8:
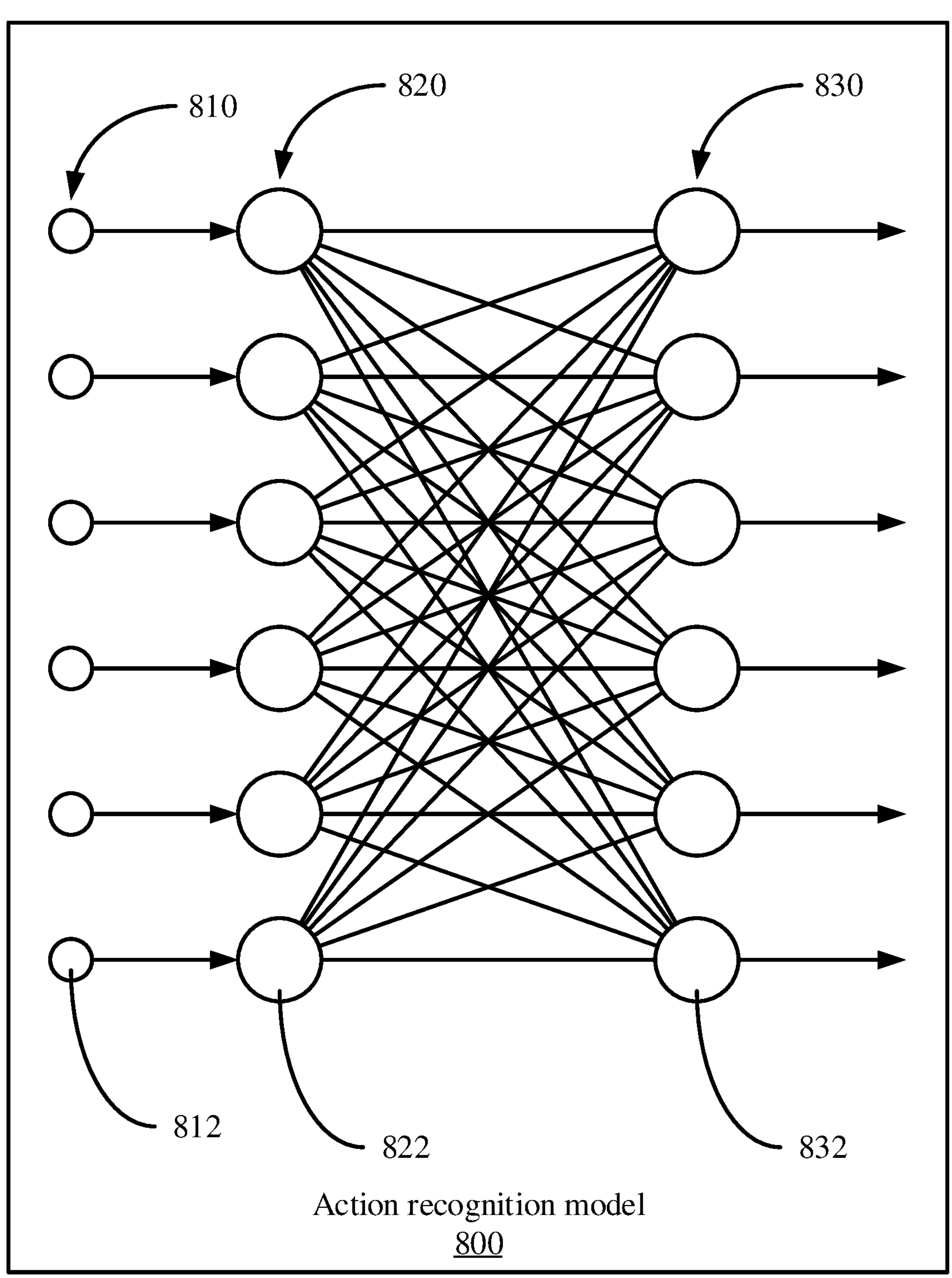
FIG. 8 is a diagram showing a neural network architecture that may be used as part of an action recognition model, in accordance with an embodiment of the present invention.
Figure 9:
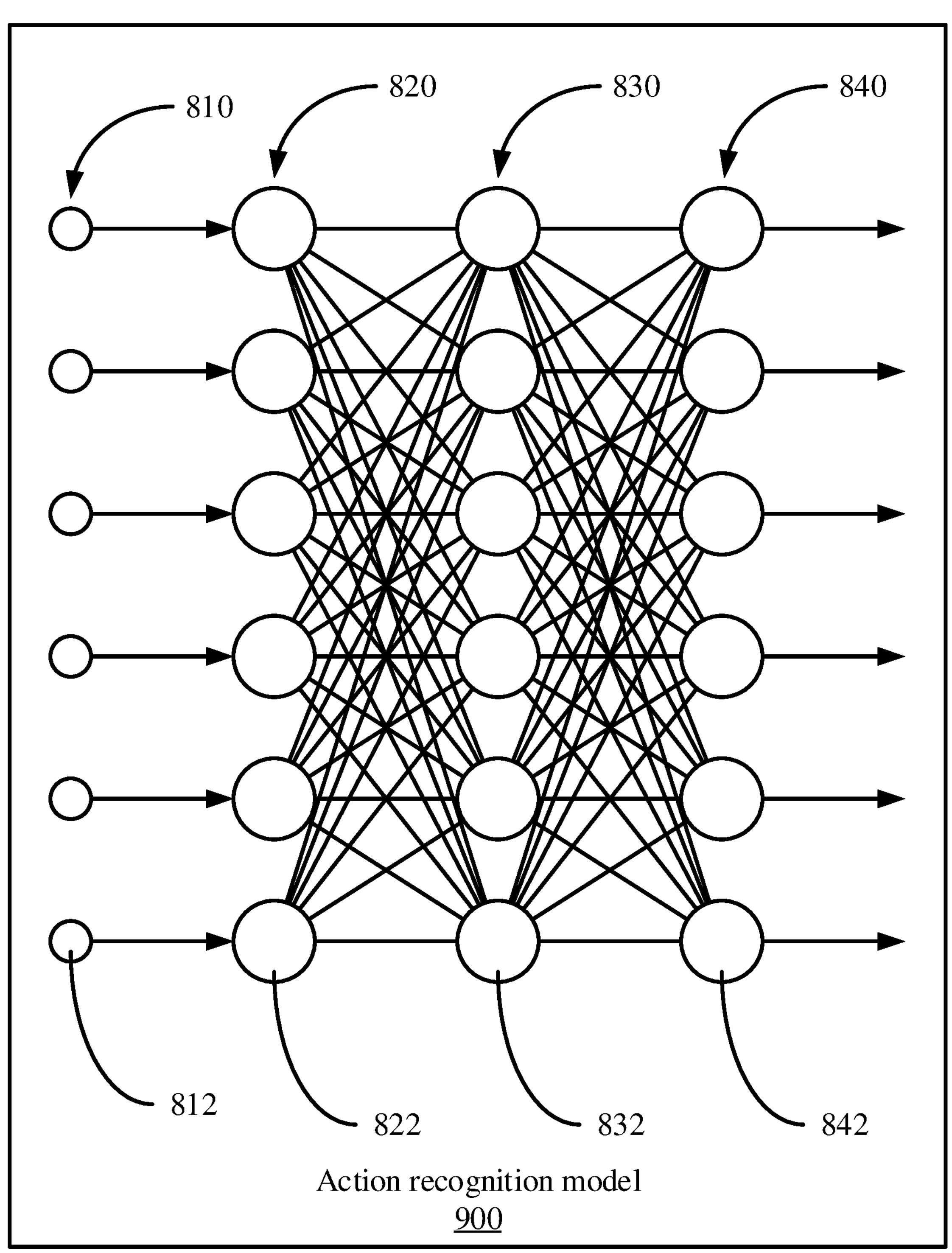
FIG. 9 is a diagram showing a neural network architecture that may be used as part of an action recognition model, in accordance with an embodiment of the present invention.

Referring now to FIGS. 8 and 9, exemplary neural network architectures are shown, which may be used to implement parts of the present models, such as action recognition models 800 and 900. A neural network is a generalized system that improves its functioning and accuracy through exposure to additional empirical data. The neural network becomes trained by exposure to the empirical data. During training, the neural network stores and adjusts a plurality of weights that are applied to the incoming empirical data. By applying the adjusted weights to the data, the data can be identified as belonging to a particular predefined class from a set of classes or a probability that the input data belongs to each of the classes can be output.

The empirical data, also known as training data, from a set of examples can be formatted as a string of values and fed into the input of the neural network. Each example may be associated with a known result or output. Each example can be represented as a pair, (x, y), where x represents the input data and y represents the known output. The input data may include a variety of different data types, and may include multiple distinct values. The network can have one input node for each value making up the example's input data, and a separate weight can be applied to each input value. The input data can, for example, be formatted as a vector, an array, or a string depending on the architecture of the neural network being constructed and trained.

The neural network "learns" by comparing the neural network output generated from the input data to the known values of the examples, and adjusting the stored weights to minimize the differences between the output values and the known values. The adjustments may be made to the stored weights through back propagation, where the effect of the weights on the output values may be determined by calculating the mathematical gradient and adjusting the weights in a manner that shifts the output towards a minimum difference. This optimization, referred to as a gradient descent approach, is a non-limiting example of how training may be performed. A subset of examples with known values that were not used for training can be used to test and validate the accuracy of the neural network.

During operation, the trained neural network can be used on new data that was not previously used in training or validation through generalization. The adjusted weights of the neural network can be applied to the new data, where the weights estimate a function developed from the training examples. The parameters of the estimated function which are captured by the weights are based on statistical inference.

In layered neural networks, nodes are arranged in the form of layers. An exemplary simple neural network has an input layer 820 of source nodes 822, and a single computation layer 830 having one or more computation nodes 832 that also act as output nodes, where there is a single computation node 832 for each possible category into which the input example could be classified. An input layer 820 can have a number of source nodes 822 equal to the number of data values 812 in the input data 810. The data values 812 in the input data 810 can be represented as a column vector. Each computation node 832 in the computation layer 830 generates a linear combination of weighted values from the input data 810 fed into input nodes 820, and applies a non-linear activation function that is differentiable to the sum. The exemplary simple neural network can perform classification on linearly separable examples (e.g., patterns).

A deep neural network, such as a multilayer perceptron, can have an input layer 820 of source nodes 822, one or more computation layer(s) 830 having one or more computation nodes 832, and an output layer 840, where there is a single output node 842 for each possible category into which the input example could be classified. An input layer 820 can have a number of source nodes 822 equal to the number of data values 812 in the input data 810. The computation nodes 832 in the computation layer(s) 830 can also be referred to as hidden layers, because they are between the source nodes 822 and output node(s) 842 and are not directly observed. Each node 832, 842 in a computation layer generates a linear combination of weighted values from the values output from the nodes in a previous layer, and applies a non-linear activation function that is differentiable over the range of the linear combination. The weights applied to the value from each previous node can be denoted, for example, by $w_1, w_2, \ldots w_{n-1}, w_n$. The output layer provides the overall response of the network to the input data. A deep neural network can be fully connected, where each node in a computational layer is connected to all other nodes in the previous layer, or may have other configurations of connections between layers. If links between nodes are missing, the network is referred to as partially connected.

Training a deep neural network can involve two phases, a forward phase where the weights of each node are fixed and the input propagates through the network, and a backwards phase where an error value is propagated backwards through the network and weight values are updated.

The computation nodes 832 in the one or more computation (hidden) layer(s) 830 perform a nonlinear transformation on the input data 812 that generates a feature space. The classes or categories may be more easily separated in the feature space than in the original data space.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment. However, it is to be appreciated that features of one or more embodiments can be combined given the teachings of the present invention provided herein.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A computer-implemented method of training a machine learning model, comprising:

identifying an object or a person related to an action in a first video to determine a bias of the machine learning model to associate the action with the object or person;

copying the object or the person from the first video to a second video to generate a third video that includes labels of the object or the person but excludes a label of the action; and training a machine learning model using the first video and the third video that mitigates the bias of the machine learning model for the action by disassociating the action with the object or the person.

2. The method of claim 1, wherein identifying the object or the person identifies a person performing the action and wherein the second video includes an environment that is different from an environment of the first video.

3. The method of claim 2, further comprising labeling the third video with a label associated with the action.

4. The method of claim 2, wherein copying the object or the person includes copying portions of frames of the first video that show the action and pasting the portions of frames onto respective frames of the second video.

5. The method of claim 1, wherein identifying the object or the person identifies an object associated with a bias of the machine learning model.

6. The method of claim 5, further comprising labeling the third video with one or more labels that exclude a label associated with the action.

7. The method of claim 5, further comprising:

training the machine learning model using the first video; and detecting the bias of the machine learning model as a false positive associated with an input that includes the object, wherein performing the identifying and copying is done responsive to detection of the bias of the machine learning model.

8. The method of claim 1, wherein the action relates to an abnormality of a patient health condition in a healthcare setting.

9. The method of claim 8, further comprising:

processing video of the patient using the machine learning model;

determining an action relating to the patient health condition; and notifying a medical professional of the patient health condition to assist the medical professional in decision-making for patient management.

10. The method of claim 9, further comprising performing a treatment action responsive to the patient health condition, including an instruction to a treatment system to automatically administer a treatment to the patient.

11. A system for training a machine learning model, comprising:

a hardware processor; and a memory that stores a computer program which, when executed by the hardware processor, causes the hardware processor to;

identify an object or a person related to an action in a first video to determine a bias of the machine learning model to associate the action with the object or the person;

copy the object or the person from the first video to a second video to generate a third video that includes labels of the object or the person but excludes a label of the action; and train a machine learning model using the first video and the third video that mitigates the bias of the machine learning model for the action by disassociating the action with the object or the person.

12. The system of claim 11, wherein the computer program causes the hardware processor to identify a person performing the action and wherein the second video includes an environment that is different from an environment of the first video.

13. The system of claim 12, wherein the computer program further causes the hardware processor to label the third video with a label associated with the action.

14. The system of claim 12, wherein the computer program further causes the hardware processor to copy portions of frames of the first video that show the action and pasting the portions of frames onto respective frames of the second video.

15. The system of claim 11, wherein the computer program further causes the hardware processor to identify an object associated with a bias of the machine learning model.

16. The system of claim 15, wherein the computer program further causes the hardware processor to label the third video with one or more labels that exclude a label associated with the action.

17. The system of claim 15, wherein the computer program further causes the hardware processor to:

train the machine learning model using the first video; and detect the bias of the machine learning model as a false positive associated with an input that includes the object, wherein the identification and copying are done responsive to detection of the bias of the machine learning model.

18. The system of claim 11, wherein the action relates to an abnormality of a patient health condition in a healthcare setting.

19. The system of claim 18, wherein the computer program further causes the hardware processor to:

process video of the patient using the machine learning model;

determine an action relating to the patient health condition; and notify a medical professional of the patient health condition to assist the medical professional in decision-making for patient management.

20. The system of claim 19, wherein the computer program further causes the hardware processor to perform a treatment action responsive to the patient health condition, including an instruction to a treatment system to automatically administer a treatment to the patient.

* * * * *